United States Patent [19]

Nesvadba et al.

[11] 4,112,091
[45] Sep. 5, 1978

[54] POLYHALO ALKYL OR ALKENYL ALCOHOL ESTERS OF PIPERAZINO ACIDS

[75] Inventors: Hans Nesvadba, Vienna, Austria; Hellmuth Reinshagen, Rheinweiler, Fed. Rep. of Germany

[73] Assignee: Sandoz Ltd., Basel, Switzerland

[21] Appl. No.: 783,989

[22] Filed: Apr. 4, 1977

[30] Foreign Application Priority Data

Apr. 9, 1976 [CH] Switzerland ............... 4529/76
Apr. 9, 1976 [CH] Switzerland ............... 4530/76

[51] Int. Cl.² .............. C07D 295/18; A61K 31/495
[52] U.S. Cl. ........................ 424/250; 544/388; 544/389; 544/391
[58] Field of Search ............... 260/268 C; 424/250

[56] References Cited

U.S. PATENT DOCUMENTS 3,733,417   5/1973   Parish et al. .................. 424/322
3,962,246   6/1976   Borer et al. ................... 260/268 C Primary Examiner—Jose Tovar
Attorney, Agent, or Firm—Gerald D. Sharkin; Robert S. Honor; Thomas O. McGovern

[57] ABSTRACT

Inhibiting methanogenesis by adding polyhaloalkyl or alkenyl alcohol esters of piperazino acids of the formula

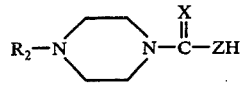

wherein X and Z are oxygen or sulphur.

11 Claims, No Drawings

POLYHALO ALKYL OR ALKENYL ALCOHOL ESTERS OF PIPERAZINO ACIDS

This invention relates to substituted piperazine derivatives. The invention provides compounds of formula

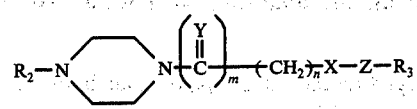   I in which
R$_2$ is hydrogen, lower alkyl, lower hydroxyalkyl or phenyl optionally substituted with one lower alkyl or hydroxyalkyl group,
Y is oxygen or sulphur,
X is a group of formula $>C=O$, $>C=S$ or —CHOH—,
Z is oxygen, sulphur or a direct bond, R$_3$ is a straight- or branched-chain alkyl or alkenyl group, which is substituted at one methyl group by two or three halogen atoms, or is an adamantyl group,
m is 0 or 1, and
n is an integer from 0 to 4, provided that when m = 0, then n = 0;
with the proviso that, when X is a group of formula —CHOH—, then m is 0, n is 1 and Z is a direct bond.

As used herein, the term "lower" in connection with alkyl or hydroxyalkyl groups means containing 1 to 4 carbon atoms. The term "halogen" means chlorine, bromine, fluorine or iodine, preferably chlorine or bromine, more preferably chlorine.

Representative compounds of formula I include those of formula Ia

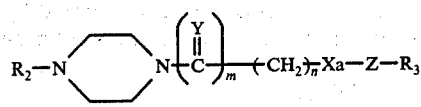   Ia in which R$_2$, R$_3$, Y, Z, m and n are as defined above, and Xa is a $>C=O$ or $>C=S$ group.

Representative compounds of formula Ia are those in which
Xa is a carbonyl group and Z is a direct bond,
Xa is a carbonyl group and Z is oxygen,
Xa is a thiocarbonyl group and Z is a direct bond, and
Xa is a thiocarbonyl group and Z is sulphur.

The preferred compounds of formula Ia are those of formula Ia'

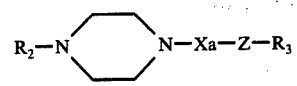   Ia' in which R$_2$, Xa, Z and R$_3$ are as defined above, particularly those in which Xa is a carbonyl group and Z is oxygen.

Further representative compounds of formula I are those of formula Ib

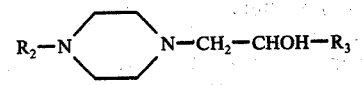   Ib in which R$_2$ and R$_3$ are as defined above.

R$_2$ is preferably hydrogen or a lower alkyl group, particularly methyl or ethyl, more particularly methyl.

A particular group of compounds of formula I are those in which R$_3$ is an adamantyl group.

R$_3$ is preferably an alkyl group, particularly a straight-chain alkyl group, suitably containing 1 to 12, preferably 1 to 6, in particular 1 or 2 carbon atoms, or an alkenyl group, preferably a straight-chain alkenyl group, suitably containing 2 to 6, preferably 2 to 4, in particular 3 carbon atoms, halogen substituted as described above.

More preferably, R$_3$ is a ω,ω,ω-trihalo- (particularly trichloro-) straight-chain alkyl of 1 to 6, preferably 1 to 2 carbon atoms, particularly trichloromethyl or 2,2,2-trichloroethyl.

The invention also provides a process for the production of compounds of formula I, characterised by
a. producing a compound of formula Ia, above by reacting a compound of formula IV

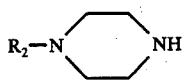   IV in which R$_2$ is as defined above, with a compound of formula V

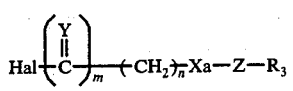   V in which Y, X$_a$, Z, R$_3$, m and n are as defined above and Hal is chlorine, bromine, iodine or fluorine, in an inert organic solvent, or b. producing a compound of formula Ib, above, by reacting a compound of formula IV with a compound of formula VI

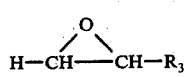   VI in which R$_3$ is as defined above, in an inert organic solvent.

Process variant (a) is carried out in conventional manner, suitably in solution in an aromatic hydrocarbon solvent, for example benzene or toluene, at room temperature or below, for example at 0° to 10° C. Process variant (b) may be carried out for example by dissolving the compound of formula VI in a suitable solvent, for example chloroform, adding the compound of formula IV and leaving to react at room temperature for a period of several days.

In both cases, the product may be isolated from the reaction mixture and purified by conventional methods.

The compounds of formula I may exist in free base form or in the form of their acid addition salts, which may be interconverted in conventional manner. The initial product of process variant (a) will normally be in the form of the hydrohalide salt.

The compounds of formula V are either known or can be prepared by conventional methods, for example by reaction of a compound of formula VII

   VII where $R_3$ and Z are as defined above, with a compound of formula VIII

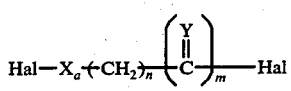
VIII where $X_a$, Y, n and m are as defined above and both Hal represent the same halogen atom.

The compounds of formulae IV, VI, VII and VIII are known.

The compounds of formula I possess nutritive activity and improve food utilisation, particularly in ruminants, in relatively low concentrations. They are therefore indicated for use as animal feed additives, in vivo by addition of the compounds to animal feed, and in vitro with the aid of an artificial rumen. In this method, substances may be tested for their inhibition of methanogenesis and/or their displacement of fatty acid formation in favour of propionate formation. Juice is taken from the rumen of a ruminant and is filtered through gauze at 39° C. while $CO_2$ is steadily bubbled through. The juice is then incubated together with the food used by the animal, which contains the test substance. After incubation, two samples are taken from the gas volume and tested, by gas chromatography, for methane and carbon dioxide. Finally, the liquid phase is tested for fatty acid content. Comparison with a sample not containing the test substance gives an activity parameter. For example, an addition of from 1 to 50 p.p.m., or even 1 to 20 p.p.m. of a compound of formula I may reduce methane production by up to 95%. At the same time the propionic acid production increases, both in absolute terms and also relative to the total fatty acid production.

The compounds of formula I are therefore useful as animal feed additives. The concentration of additive in the animal feed will of course vary, for example depending on the compound used. However, in general, satisfactory results are obtained when the compound of formula I is present in the feed at a concentration of 0.1 to 100 mg per kg of foodstuff. The compounds may be used in free base form or in the form of their physiologically acceptable acid addition salts, for example their hydrochlorides.

For this use, i.e. as a nutritional aid, the compounds of formula I may also be administered in the form of veterinary compositions such as tablets, boluses, capsules or aqueous solutions for addition to drinking water. Such dosage forms may be produced in conventional manner. The dosage to be administered in such manner will be dependent on food consumption and can be calculated from the concentration range mentioned above.

The most preferred compounds of formula I include 4-methylpiperazine-1-carboxylic acid 2,2,2-trichloroethyl ester and 1-methyl-4-(3,3,3-trichloro-2-hydroxypropyl) piperazine.

The following examples illustrate the invention:

EXAMPLE 1

4-Methylpiperazine-1-carboxylic acid 2,2,2-trichloroethyl ester. (Process variant a))

N-methylpiperazine (2 g) is dissolved in 20 ml benzene and reacted with a solution of 4.5 g 2,2,2-trichloroethyl chloroformate in 20 ml benzene, with stirring and cooling in an ice bath. After stirring for 2 hours the resulting crystals are collected by vacuum filtration, washed with ether and dried under water-pump vacuum at room temperature, to give the hydrochloride of the title compound, m.p. 238°–240° C.

EXAMPLE 2–10

In manner analogous to Example 1, and employing appropriate starting materials in approximately equivalent amounts, the following compounds may be obtained:

2. 1-methyl-4-dichloroacetylpiperazine hydrochloride, m.p. 218°–223° C.;
3. 1-methyl-4-trichloroacetylpiperazine hydrochloride, m.p. 234°–236° C.
4. piperazine-1-carboxylic acid 2,2,2-trichloroethyl ester hydrochloride;
5. 4-(2-hydroxyethyl)piperazine-1-carboxylic acid 2,2,2-trichloroethyl ester hydrochloride;
6. 1-methyl-4-(2-trichloromethylpropionyl) piperazine hydrochloride;
7. 1-methyl-4-(4,4,4-trichlorocrotonoyl)piperazine hydrochlorde;
8. 1-methyl-4-(7,7,7-trichloro-6-oxo-heptanoyl)piperazine hydrochloride;
9. 1-methyl-4-adamantoylpiperazine hydrochloride;
10. 4-methylpiperazine-1-carbodithioic acid 2,2,2-trichloroethyl ester hydrochloride;

EXAMPLE 11

1-Methyl-4-(3,3,3-trichloro-2-hydroxypropyl) piperazine (process variant b))

N-methyl piperazine (2 g) is dissolved in 80 ml chloroform, and mixed with a solution of 3.22 g 3,3,3-trichloropropylene oxide in 20 ml chloroform. The mixture is allowed to stand at room temperature for 6 days. The chloroform is removed by evaporation, and ether is added to the residue, which is then collected by filtration, washed with ether and dried at room temperature under water pump vacuum, to give the heading compound, m.p. 165°–167° C.

EXAMPLE 12,13

In manner analogous to Example 11, and employing appropriate starting materials in approximately equivalent amounts, the following compounds may be obtained:

12. 1-phenyl-4-(3,3,3-trichloro-2-hydroxypropyl)piperazine;
13. 1-p-tolyl-4-(3,3,3-trichloro-2-hydroxypropyl)piperazine.

What is claimed is:
1. A compound of formula I

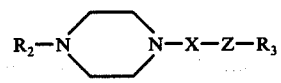
I in which
$R_2$ is hydrogen, lower alkyl, lower hydroxyalkyl, phenyl, mono lower alkyl phenyl or monohydroxy lower alkyl phenyl,
X is a group of formula $>C=O$ or $>C=S$,
Z is oxygen or sulphur, and
$R_3$ is a straight- or branched-chain alkyl of 1 to 12 carbon atoms or an alkenyl group of 2 to 6 carbon atoms, which is substituted at one methyl group by two or three halogen atoms.

2. A compound of claim 1 in which X is a carbonyl group and Z is oxygen.

3. A compound of claim 1 in which $R_2$ is hydrogen or an alkyl group having from 1 to 4 carbon atoms.

4. A compound of claim 3 in which $R_2$ is methyl.

5. A compound of claim 1 in which $R_3$ is a $\omega,\omega,\omega$-trichloro-straight-chain alkyl group of 1 to 6 carbon atoms.

6. A compound of claim 5 in which $R_3$ is a trichloromethyl or 2,2,2-trichloroethyl group.

7. The compound of claim 1 which is 4-methylpiperazine-1-carboxylic acid 2,2,2-trichloroethyl ester.

8. A method of improving animal feed utilisation comprising administering an effective amount of a compound of claim 1.

9. The method of claim 8 in which the compound is administered in admixture with the animal feed.

10. An animal feed containing a compound of claim 1, in free base form or in physiologically acceptable acid addition salt form, in an amount effective to improve food utilisation.

11. An animal feed of claim 10, containing from 0.1 to 100 mg of the compound per kg of foodstuff.

* * * * *